United States Patent [19]
Nishimura et al.

[11] Patent Number: 5,282,030
[45] Date of Patent: Jan. 25, 1994

[54] ENDOSCOPIC IMAGE PROCESSOR AND ENDOSCOPIC IMAGE PROCESSING METHOD

[75] Inventors: Hirokazu Nishimura, Hachioji; Tetsuo Nonami, Tama; Masakazu Nakamura, Hachioji, all of Japan

[73] Assignee: Olympus Optical Co., Ltd., Tokyo, Japan

[21] Appl. No.: 847,993

[22] PCT Filed: Nov. 18, 1991

[86] PCT No.: PCT/JP91/01576
§ 371 Date: Apr. 8, 1992
§ 102(e) Date: Apr. 8, 1992

[87] PCT Pub. No.: WO92/08405
PCT Pub. Date: May 29, 1992

[30] Foreign Application Priority Data
Apr. 12, 1991 [JP] Japan .................. 3-079606
Nov. 19, 1991 [JP] Japan .................. 2-313376

[51] Int. Cl.$^5$ .............. H04N 9/68; H04N 9/69; H04N 9/73; H04N 9/77
[52] U.S. Cl. ................ 348/71; 358/527; 348/29; 348/242; 348/421
[58] Field of Search ........ 358/98, 36, 37, 80, 358/133, 13; H04N 9/68, 9/69, 9/73, 9/77, 7/133

[56] References Cited

U.S. PATENT DOCUMENTS
4,819,077 4/1989 Kikuchi .................. 358/80
4,845,553 7/1989 Konomura et al. .......... 358/98

FOREIGN PATENT DOCUMENTS
323362 7/1989 European Pat. Off. .

OTHER PUBLICATIONS
Week 8450, Research Disclosure Nov. 1984, 24750, Anonymous, "Noise Reduction in Multi-Band Image Data".
Patent Abstracts of Japan, Dec. 18, 1989, vol. 13, No. 570, 1-238650.
Patent Abstracts of Japan, Nov. 6, 1989, vol. 13, No. 486, 1-192270.

*Primary Examiner*—Howard W. Britton
*Attorney, Agent, or Firm*—Armstrong, Westerman, Hattori, McLeland & Naughton

[57] ABSTRACT

A group of vectors are set to transform each signal of an endoscopic image resolved into a plurality of color signals into a plurality of new color signals based on statistical characteristics of the image. Also, the color signals of the endoscopic image are transformed into new color signals by a matrix operation using the group of vectors for the new color signals. After filtering is applied to the plurality of new color signals, the plurality of new color signals are transformed into a plurality of original color signals by a matrix operation using an inverse matrix of the matrix used in the matrix operation.

25 Claims, 14 Drawing Sheets

SHADED PART REPRESENTS
A BAND TO BE PASSED

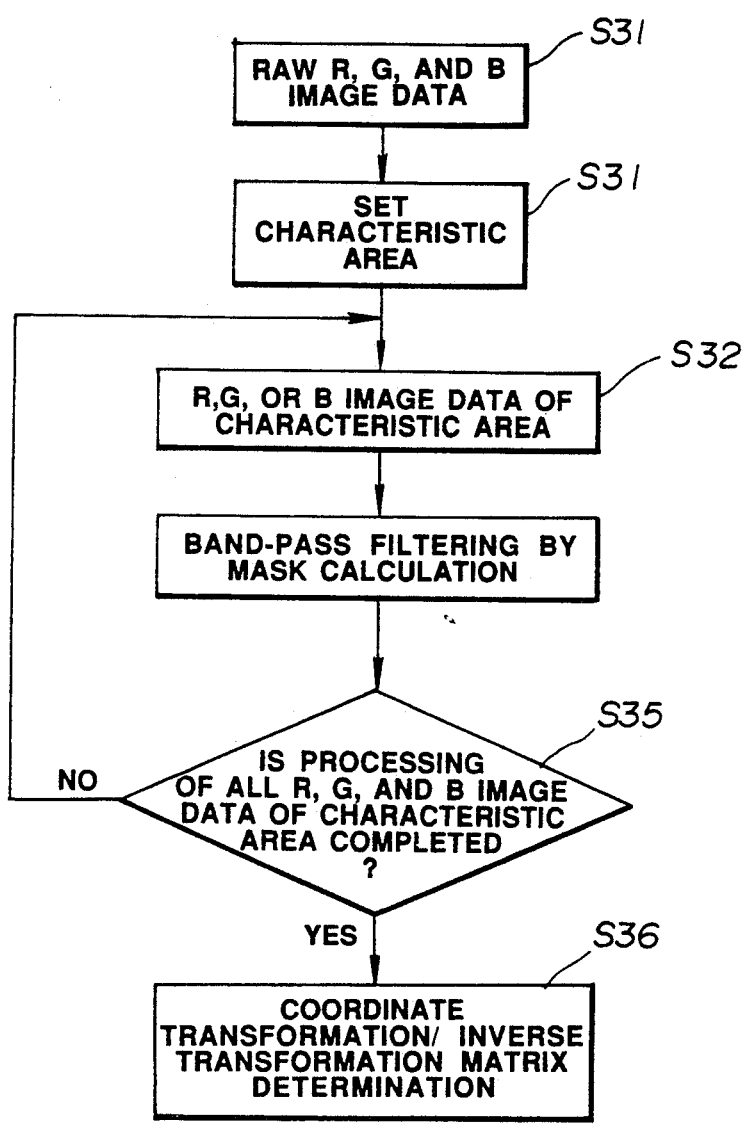

5,282,030

ENDOSCOPIC IMAGE PROCESSOR AND ENDOSCOPIC IMAGE PROCESSING METHOD

BACKGROUND OF THE INVENTION

1. Field of the Invention

The present invention relates to an endoscopic image processor for filtering endoscopic image data properly resolved into a plurality of color signals, and to its image processing method.

2. Description of the Related Art

Endoscopes have come to be widely adopted in recent years. Using an endoscope, a lesion in a body cavity can be observed or, if necessary, treated using a treatment tool merely by inserting the elongated insertion tube into the body cavity without requiring an incision.

Among the aforesaid endoscopes, an optical endoscope (for example, a fiberscope) using an image guide as image transfer means as well as an electronic endoscope (thereafter, electronic scope or scope) using a solid state imaging device, such as a CCD, has been put to practical use.

In another fiberscope, an imaging camera using a solid state imaging device, such as a CCD, is connected to the eyepiece part of the fiberscope so that images can be displayed in color on the monitor.

Moreover, attempts are being made recently to process video signals obtained from this kind of endoscopes in various ways, and thus assist human beings in recognizing things eventually improving the diagnostic capability of the endoscopes.

For example, according to U.S. Pat. No. 4,819,077, an apparatus is disclosed. In the apparatus, red, green and blue (R, G and B) video signals which indicate three primary colors are converted into signals of the hue, saturation and intensity (H,S and I) relatively close to human color perception by performing relatively simple coordinate transformation. Then, the H, S and I signals are enhanced appropriately, then returned to R, G and B signals by performing inverse transformation. Finally, the results are displayed.

Moreover, according to Japanese Patent Laid Open No. 138877/1989, an apparatus is disclosed. In the apparatus, image signals are converted into a Lu* v* color space which is further close to human color perception, then subjected to a variety of enhancement. Then, inverse transformation is carried out.

In Japanese Patent Laid Open No. 26783/1988, the applicant discloses an apparatus which converts video signals into signals in the Lab* b* or Lu* v* color space and enhances intensity L.

In these endoscopes of the prior art, high-frequency components of intensity are enhanced to intensify the contour of a color image or fine patterns. This is because when intensity is disconnected from hue or saturation, enhancement can be done without varying color tone. On the contrary, when each plane of R, G and B signals is enhanced independently, color tone varies resulting in unnatural images.

In endoscopic observation of living bodies, depending on the object to be observed, the endoscope may not provide sufficient observation capability of resolution, brightness and contrast because of mechanical restrictions. In particular, even if an endoscope offering highest resolution available at present is used to observe a fine pattern on the mucosal surface (formed by a glandular cavity of the gastric gland or intestinal gland, an innominate fossa, a capillary, or stein) or an important finding for differentiating a malignant lesion from benign lesions, images having satisfactory quality for diagnosis cannot always be obtained.

Therefore, an endoscope offering higher resolution is greatly desirable. Also, desirable are an image processing procedure which compensates for insufficient contrast or resolution and helps simplify clinical evaluation and an apparatus in which the procedure is implemented.

For example, in ordinary endoscopic images (obtained without using stain), a fine pattern in a mucosal surface is visualized by detecting the variations of G and B signals as variation information forming the pattern. This, presumably, reflects the light absorbing property of hemoglobin in blood.

Images obtained using stain are subject to not only reflection or absorption intrinsic to living bodies but also absorption by stain. These properties determine data variations forming an image.

Conventional high-frequency enhancement in a color space cannot enhance these images successfully. The underlying reason may be as mentioned below.

Data distribution derived from data variations forming a fine pattern is inconsistent with the variation of any one of intensity, hue and saturation in human color perception.

An observer acquires overall information from an image first. Next, he/she observes a fine pattern meticulously in an attempt of acquiring more detailed information. In this stage, the observer concentrates on some information attributable to the living body contained in the image. It has no significant meaning to the observer whether the information is expressed by intensity, saturation or hue.

A well accepted enhancement procedure, which assists an observer, would amplify data variations noted in a region of interest but suppress the other data variations. Enhancement in a color space cannot always satisfy this condition.

Therefore, enhancement in a color space does not always provide an observer of a fine pattern with optimal results.

In addition, data variations in an entire endoscopic image are prone to general variations resulting from lighting or the shape of an object. Intensity enhancement tends to highlight a contour formed by the general variations more clearly. This makes it difficult to observe fine patterns.

SUMMARY OF THE INVENTION

The principal object of the present invention is to provide an endoscopic image processor permitting accurate observation of fine patterns in the mucosal surface of a living body, and its image processing method.

Another object of the invention is to provide an endoscopic image processor setting an appropriate filter function according to the structural pattern of a raw endoscopic image to suppress noise and enhance a required structure to display it clearly, and its image processing method.

Another object of the invention is to provide an endoscopic image processor transforming the coordinates of R, G and B endoscopic image data, setting a filter function supressing noise and having an enhancing effect on each axis, then filtering each image transformed into each axis data, and its image processing method.

Another object of the invention is to provide an endoscopic image processor capable of enhancing a normal endoscopic image without being stained and a stained endoscopic image properly, and its image processing method.

Another object of the invention is to provide an endoscopic image processor capable of extracting a characteristic area from endoscopic images manually or automatically (by executing a program) and passing only the image data in a frequency band containing the largest number of characteristic components in an endoscopic image among the images of the extracted characteristic area, extracting only the characteristic components from the raw image and adaptively performing coordinate transformation enhancing the characteristic components effectively, and its image processing method.

An endoscopic image processor according to the present invention comprises color signal transforming means for setting a vector group for transforming each signal of an endoscopic image decomposed into a plurality of color signals into a plurality of new color signals based on statistical characteristics of the image and transforming the color signal of the endoscopic image into new color signals by a matrix operation using the vector group, filtering means for filtering the plurality of new color signals produced by the color signal transforming means and means for transforming the plurality of new color signals after the filtering means applied filtering to the new color signals into a plurality of original color signals by the matrix operation using an inverse matrix of the matrix used for the matrix operation.

An endoscopic image processing method of the invention comprises a color signal transforming step of setting a vector group for transforming each signal of an endoscopic image decomposed into a plurality of color signals into a plurality of new color signals based on statistical characteristics of the image and transforming the color signals of the endoscopic image into new color signals by a matrix operation using the vector group, a filtering step of filtering the plurality of new color signals produced by the color signal transforming step and a step of transforming the plurality of new color signals after the filtering step applied filtering to the new color signals into a plurality of original color signals by the matrix operation using an inverse matrix of the matrix used for the matrix operation.

BRIEF DESCRIPTION OF THE DRAWINGS

FIG. 1 is a block diagram showing the structure of an endoscope system;

FIG. 2 is a block diagram showing the structure of an image processor;

FIG. 3 is an explanatory diagram showing the entire endoscope system;

FIG. 4 is a flowchart helping explain a processing method using the image processor;

FIG. 5 is an explanatory diagram showing a weighting function used for filtering;

FIGS. 7 to 16 show an image processing method according to the third embodiment of the invention;

FIGS. 7 and 8 are flowcharts showing the image processing method;

FIG. 9 is a flowchart showing a characteristic area setting step of FIG. 8;

FIG. 10 is a flowchart showing a band-pass filtering step of FIG. 8;

FIG. 11 is an explanatory diagram showing correlational distribution of R and G data values on a picture plane;

FIG. 12 is an explanatory diagram showing an example of correlational distribution of the R and G data values of FIG. 11 after band-pass filtering;

FIGS. 14 and 15 are explanatory diagrams showing band-pass filtering;

FIG. 16 is an explanatory diagram showing an example of setting a characteristic area automatically; and FIGS. 17 and 18 are flowcharts showing variations using a mask operation processing method by a convolution in place of a Fourier function and a process using a weighting function.

DETAILED DESCRIPTION OF THE PREFERRED EMBODIMENTS

FIGS. 1 to 5 show an endoscopic image processor according to the first embodiment of the invention.

Figure 3:
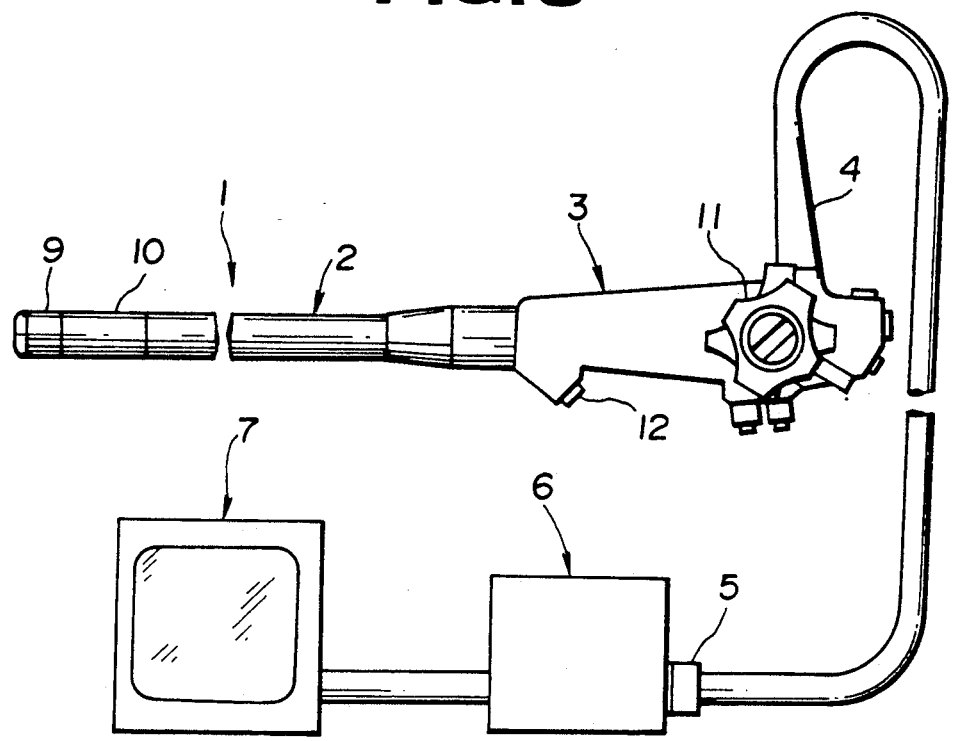

An endoscope system according to the embodiment has an electronic endoscope, as shown in FIG. 3. The electronic endoscope 1 includes an elongated and, for example, flexible insertion tube 2. An operation unit 3 is connected to the end of the insertion tube 2. A flexible universal cord 4 is extending laterally from the end of the operation unit 3. A connector 5 is attached to the tip of the universal cord 4. The electronic endoscope 1 is connected to a video processor 6 incorporating a light source and a signal processing circuit via the connector 5. A monitor 7 is connected to the video processor 6.

The insertion tube 2 includes a rigid distal end 9 at the tip and a bending section 10 which is adjoining to the distal end 9 and capable of bending backward. By turning a bending operation knob 11 installed at the operation unit 3, the bending section 10 can be bent laterally or vertically. The operation unit 3 has an inlet 12 leading to a treatment adapter channel installed inside the insertion tube 2.

Figure 1:
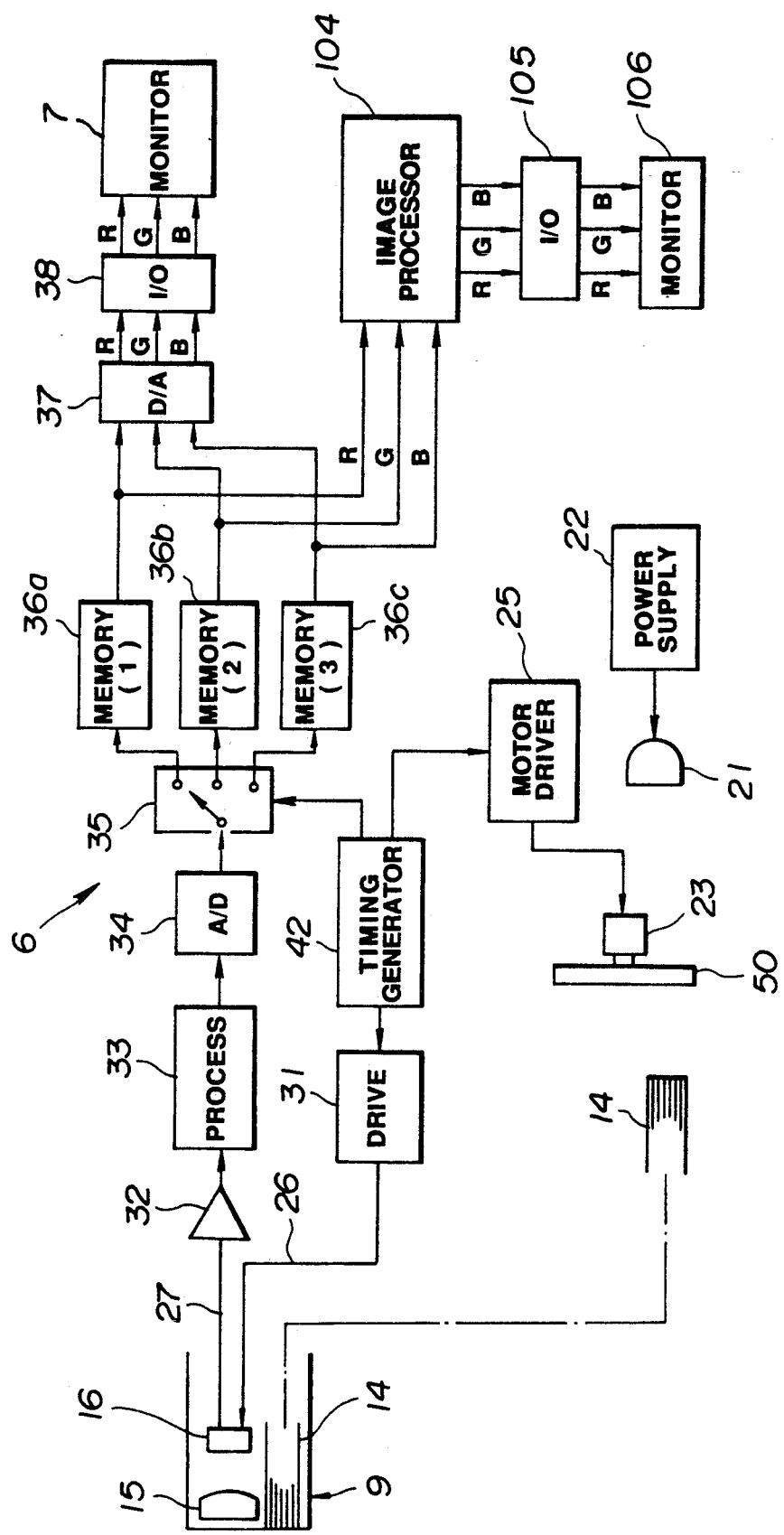
FIGS. 1 to 5 show an endoscopic image processor and its image processing method according to the first embodiment of the present invention.

As shown in FIG. 1, a light guide 14 for transmitting light is traveling inside the insertion tube 2 of the electronic endoscope 1. The tip surface of the light guide 14 is aligned with the distal end 9 of the insertion tube 2, so that light can be emitted from the distal end 9. The incident end of the light guide 14 is connected to the connector 5 by passing through the universal cord 4. In the distal end 9, an object lend 15 is installed and a solid state imaging device 16 is arranged at the image forming position of the object lens 15. The solid state imaging device 16 is sensitive in a wide range of wave lengths including a visible region and extending from an ultraviolet region to an infrared region. To the solid state imaging device 16, signal lines 26 and 27 are connected. The signal lines 26 and 27 are connected to the connector 5 by passing through the insertion tube 2 and universal cord 4.

On the other hand, the video processor 6 incorporates a lamp 21 emitting a wide band light from ultraviolet light to infrared light. An ordinary xenon lamp or strobe light can be employed as the lamp 21. The xenon lamp or strobe light emits a large amount of visible light as well as ultraviolet and infrared light. The lamp 21 is supplied power by a power supply 22. A rotation filter 50 driven by the rotation of a motor 23 is installed in the front of the lamp 21. In the rotation filter 50, filters for transmitting light of red(R), green(G) and blue(B) wavelength regions are arranged in the circumferential direction of the filter 50.

The rotation of the motor 23 is controlled and driven by a motor driver 25.

Light separated time-sequentially into light of R, G and B wavelength regions is transmitted to the incident end of the light guide 14, led to the distal end 9 via the light guide 14, then emitted from the distal end 9 to illuminate a region to be observed.

Light returning from the observation region forms an image on the solid state imaging device 16 and is converted into electric signals. The solid state imaging device 16 is applied drive pulses sent from a drive circuit 31 in the video processor 6 over the signal line 26. With a drive pulse, a signal is read out or transferred. A video signal read out from the solid state imaging device 16 is input to a preamplifier 32 installed in the video processor 6 or electronic endoscope 1 over the signal line 27. The video signal amplified by the preamplifier 32 is input to a process circuit 33, subjected to gamma correction or white balancing, then converted into a digital signal by an A/D converter 34. The digital video signal is stored selectively in, for example, a memory (1) 36a, memory (2) 36b and memory (3) 36c corresponding to red(R), green(G) and blue(B) light by a select circuit 35. The memory (1) 36a. memory (2) 36b and memory (3) 36c are read simultaneously. Then, the data is converted into analog signals by a D/A converter 37, input as R, G and B signals to a color monitor 7 via an input-output interface 38. Then, the observation region is displayed in color on the color monitor 7.

The video processor 6 incorporates a timing generator 42 for producing timing for the entire system. The timing generator 42 synchronizes the motor driver 25, drive circuit 31 and select circuit 35.

In this embodiment, the outputs of the memories (1) 36a to (3) 36c are connected to an image processor 104. The image processor 104 is connected to a monitor 106 via an input-output interface 105. The results of arithmetic operation by the image processor 104 are displayed on the monitor 106.

Figure 2:
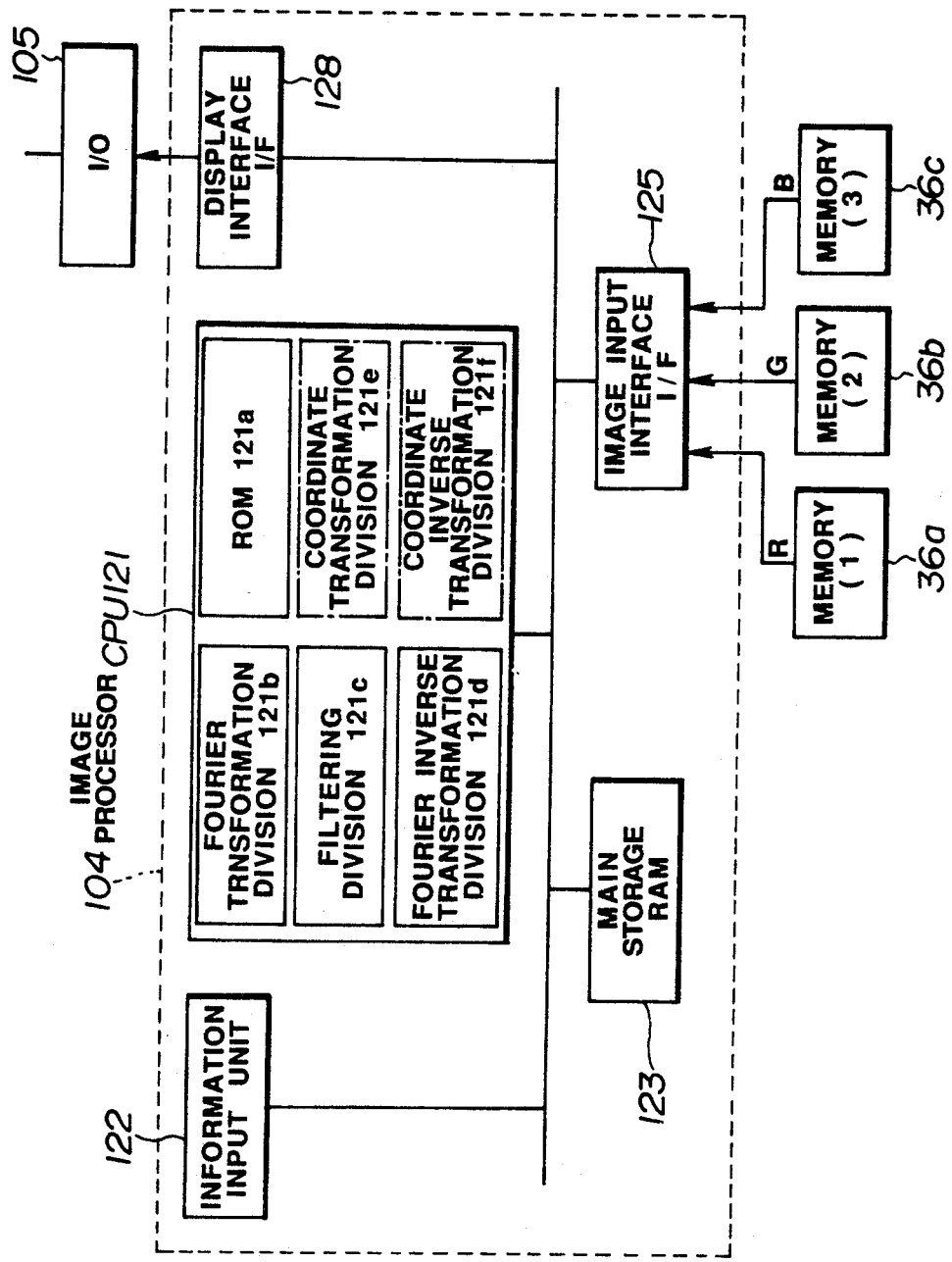

The image processor 104 has a configuration shown in FIG. 2.

The image processor 104 comprises a CPU 121, an information input unit 122, a main storage 123 consisting of RAM, an image input interface 125 and a display interface 128. These devices are mutually connected over a bus. The information input unit 122 is a keyboard or the like for entering a type of the electronic endoscope 1 and other data. The image input interface 125 is connected to the memory (1) 36a, memory (2) 36b and memory (3) 36c, and receives image data from the memories. The display interface 128 is connected to the input-output interface 105, and transmits image data to the monitor 106.

The CPU 121 comprises a ROM 121a containing a series of image processing programs which is described later, a Fourier transformation division 121b for applying two-dimensional Fourier transformation to endoscopic image signals decomposed into a plurality of color signals, for example, R, G and B signals in order to generate a real term and an imaginary term, a filtering division 121c for weighting the generated real and imaginary terms using a weighting function and a Fourier inverse transformation division 121d for applying two-dimensional Fourier inverse transformation to the weighted real and imaginary terms in order to generate weighted color signals. The main storage (RAM) can be connected to hard disk regenerating/recording unit (not illustrated) or other external recorder. In the main storage, a variety of weighting functions supplied from the external recorder are sorted and used for weighting in the filtering division 121b of the CPU 121.

In this embodiment, an image of an object region acquired by an electronic endoscope 1 is processed by an image processor 104, then the processed results are output to a monitor 106.

The operations of the image processor 104 are explained below.

Figure 4:
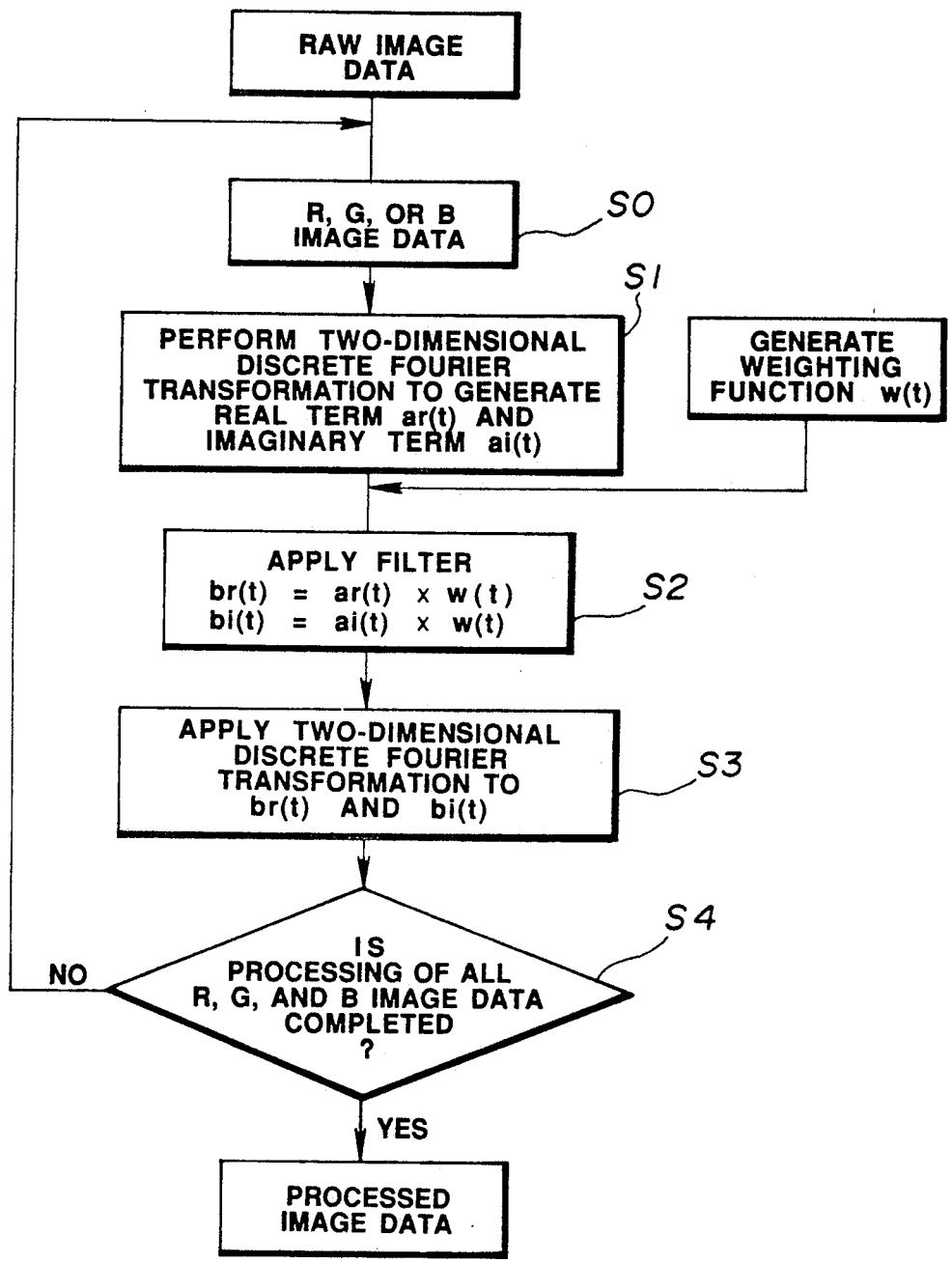

In the first embodiment, the image processor 104 carries out the operation shown in FIG. 4.

A raw image is decomposed into R, G and B color signals at a step S0 or a step prior to inputting into the image processor 104. The R, G and B color signals are stored in memories (1) 36a to (3) 36c. For the R, G and B image signals, two-dimensional discrete Fourier transformation is performed to generate a real term ar (t) and an imaginary term ai (t) at a step S1.

Next, at a step S2, filtering (process) is performed to multiply the real term ar (t) and imaginary term ai (t) or data generated by two-dimensional discrete Fourier transformation at the step S1 by a weighting function w (t). As a result, the real term br (t) and imaginary term bi (t) of a filtered function are generated.

The weighting function w (t) optimizes the R, G and B image signals respectively. Specifically, for an ordinary endoscopic image acquired without using stain, the R image signal is subjected to noise suppression filtering for performing noise suppression. However, the G and B image signals are processed with a weighting function for performing enhancement filtering. After filtering is completed, two-dimensional discrete Fourier inverse transformation is performed at a step S3. As a result, an enhanced R, G or B image signal is generated. Then, at a step S4, it is checked if processing of all R, G and B image signals is completed. If not completed, the steps S0 to S3 are repeated until all R, G and B image signals have been processed. When enhanced R, G and B image signals are generated, they are transferred to a monitor 106 via an input-output interface 105. Then, the resultant image is displayed on the monitor 106. Thus, the image processing terminates. The digital R, G and B image signals are converted into analog signals by a D/A converter if necessary.

A weighting function used for the aforesaid filtering is generated as mentioned below. In so-called optical Fourier transformation, DC components which determine an overall density of an image is positioned in the center of a spatial-frequency plane. Low-frequency components relative to spatial frequencies reside in the vicinity of the DC components. A filter is created shall give the greatest weight to a point at a distance from the center and reduce the weighting level for low-frequency and high-frequency components gradually from a boundary of the point. The weighting function having this property is conceivable in various types. The filter described below is an example of the weighting function.

When the coordinates of the center O in a spatial-frequency plane is (u0, v0), and those of a point P on the same plane, (u,v), the distance t of OP is expressed as $$t = ((u-u0)^2 + (v-v0)^2)^{\frac{1}{2}}.$$

When a weighting value w is expressed as a function w(t) of t, the w(t) value is equal to or greater than 0, and equal to or smaller than α, wherein α denotes a maximum weighting value. When the center of a circle formed by a set of points yielding a maximum w(t) value is 0 and the diameter is p, the filter to be created consists of two different functions for use under the conditions of $0 \leq t < p/2$ and $p/2 \leq t$ respectively. A cos function is used in $0 \leq t < p/2$, while a normal distribution function is used in $p/2 \leq t$.

In the cos function division of the filter to be created, A is specified as the amplitude. The cos function division shall be continuous at $t = p/2$ for the normal distribution function, and shall meet $w(p/2) = \alpha$. The w(t) must yield a minimum value with $t = 0$. A formula (a) is obtained as a function meeting these conditions below.

$$w(t) = \alpha - A - A \times \cos(t \times \pi/(p/2)) \quad (0 \leq t < p/2) \tag{a}$$

The function of the formula (a) provides a maximum α with $t = p/2$ and a minimum $\alpha - 2A$ with $t = 0$ (center in a spatial-frequency domain).

On the other hand, the normal distribution function division yields the maximum α and is continuous at $t = p/2$ for the cos function division. Assuming that a standard deviation in this kind of function is σ, a formula (b) is, obtained below:

$$w(t) = \alpha \times \exp(-0.5((t-(p/2)/r)/\sigma)^2) \quad (p/2 \leq t) \tag{b}$$

In the formula (b), σ is given as $\sigma = (CTR - (p/2)/r$ (where, CTR represents an x-coordinate value of the center, and r, a real number). When p is 0, only the formula (b) is adopted.

Figure 5:
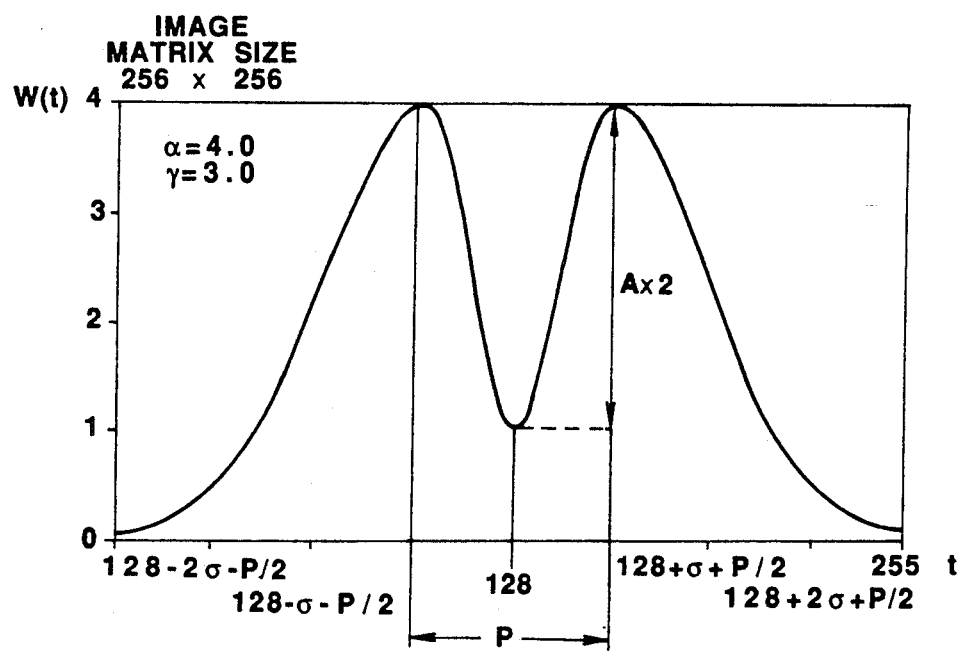

In the formulas (a) and (b), when α, A, p and r are specified as parameters, filters with different enhancement levels can be obtained. FIG. 5 shows a slope of a filter created under the foregoing conditions, wherein $\alpha = 4$, $A = 1.5$, $p = 60$ and $r = 4$. To realize filtering permitting a noise suppression effect, high-frequency components which are thought to contain many noise components must be suppressed. For example, 1 should be specified as α, 0 as A, 0 as p and 3 as r. To realize filtering permitting an image enhancement effect, a frequency band which is thought to contain a large amount of structural pattern information of raw image must be enhanced, and frequency components which are higher than the band, be suppressed. For example, 3 should be specified as α, 1 as A, 50 as p and 4 to 7 as r.

According to the first embodiment, R, G and B image signals are decomposed into spatial-frequency components, then a filter function having a function for suppressing spatial-frequency noise or an enhancement function is set to filter image signals decomposed into spatial-frequency components. Therefore, when a filter function is set appropriately according to a structure pattern of raw image data, noise is suppressed successfully to visualize an intended structure clearly. This improves the clinical value of endoscopic images.

Next, the second embodiment of the invention is explained.

Figure 6:
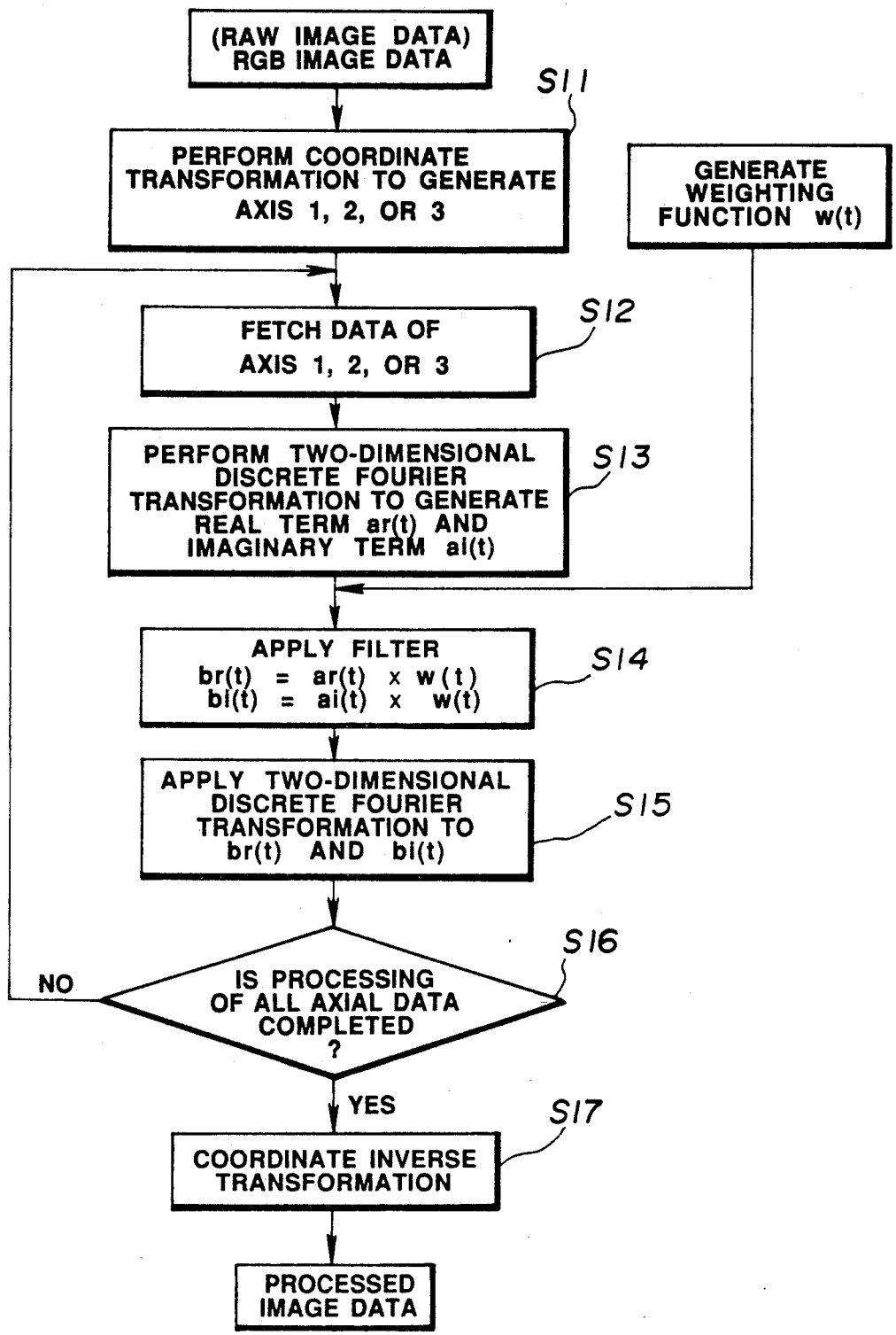
FIG. 6 is a flowchart helping explain an image processing method according to the second embodiment of the invention.

The configuration of an endoscope system according to the second embodiment is identical to that according to the first embodiment. The configuration of an image processor 104 of the second embodiment is substantially identical to that of the first embodiment. The processing contents, however, differ from those shown in FIG. 4. FIG. 6 shows the processing flow.

In this embodiment, a CPU 121 incorporated the image processor 104 has a coordinate (axis) transformation division 121e and a coordinate (axis) inverse transformation division 121f, which are indicated with an alternate long and short dash line in FIG. 2, in addition to the components of the first embodiment. The coordinate (axis) transformation division 121e performs coordinate (axis) transformation to convert endoscopic image signals decomposed into a plurality of R, G and B color signals into the axial data of three axes (for example, axis ①, axis ② and axis ③, or x-axis, y-axis and z-axis). Also, each of the aforesaid axes is, for example, selected to set through the CPU 121 by the data retrieved from an information input unit 122. Then, the data setting these axes can be stored in, for example, a main storage 123 from the outside. The coordinate (axis) inverse transformation division 121f performs inverse transformation to return the axial data into R, G and B color signals.

As shown in FIG. 2, R, G and B image data stored in memories (1) 36a to (3) 36c are subjected to coordinate transformation at a step S11 as shown in FIG. 6. At the step S11, the R, G and B image data are processed to generate data of axes ①, ② and ①. Then, at a step S12, the axial data is fetched. At a step S13, two-dimensional discrete Fourier transformation is performed on the fetched data to generate a real term ar(t) and an imaginary term ai(t).

The real term ar(t) and imaginary term ai(t) are filtered according to a weighting function w(t) in the same manner as described for the first embodiment at a step S14. As a result, a real term br(t) and an imaginary term bi(t) for a filtered function are generated. Then, the real term br(t) and imaginary term bi(t) undergo two-dimensional discrete Fourier inverse transformation at a step S15. At a step S16, it is checked if processing of all axial data is completed. When all axial data completes the steps S12 to S15, coordinate inverse transformation is performed at a step 17. Then, the resultant image is displayed on a monitor 106.

An example of coordinate transformation performed at the step S11 is represented as a formula (c) or (c').

$$M1 \times M2 = M3 \tag{c}$$

that is:

$$\begin{pmatrix} 0 & 1 & 1 \\ 0 & 1 & -1 \\ 1 & 0 & 0 \end{pmatrix} \begin{pmatrix} r \\ g \\ b \end{pmatrix} = \begin{pmatrix} ① \\ ② \\ ③ \end{pmatrix} \tag{c'}$$

where, M1 denotes a coordinate transformation matrix, M2, a matrix of R, G and B image signals, and M3, a matrix of axes ①, ② and ③ which is generated by coordinate transformation.

Then, the aforesaid filter is applied to coordinate axes newly generated according to the coordinate transformation matrix M1. Specifically, filtering for enhancing only the axis 1 is applied. For the axes 2 and 3, filtering performing a noise suppression effect is employed. Alternatively, filtering performing an enhancement effect is applied to the axes 1 and 2. For the axis 3, filtering having a noise suppression effect is employed. Coordinate inverse transformation is implemented by applying an inverse matrix M4 of the matrix M1 according to a formula (d) or (d').

$$M4 \times M5 = M6 \qquad (d)$$

that is:

$$\begin{pmatrix} 0 & 0 & 1 \\ \frac{1}{2} & \frac{1}{2} & 0 \\ \frac{1}{2} & -\frac{1}{2} & 0 \end{pmatrix} \begin{pmatrix} ① \\ ② \\ ③ \end{pmatrix} = \begin{pmatrix} r' \\ g' \\ b' \end{pmatrix} \qquad (d')$$

where, M4 denotes an inverse matrix for the coordinate transformation matrix M1, M5, a matrix of enhanced data, and M6, a matrix of enhanced R, G and B image signals.

The coordinate transformation matrix M1 is employed for normal endoscopic image. For enhancement of an image acquired using stain, a different coordinate transformation matrix may be applied. Further, the coordinate transformation matrix may differ with the type of image data.

The second embodiment offers almost the same effects as the first embodiment. Coordinate transformation may permit filtered images capable of visualizing an intended structure more clearly.

The parameter values of a weighting function w(t) used for filtering may be varied sequentially, so that the processed image can be displayed or recorded sequentially. This allows the operator to select any processed data or processed image data capable of visualizing an intended region most clearly.

FIGS. 7 to 17 show an image processing method according to the third embodiment. The image processor explained for the second embodiment is employed.

Figure 7:
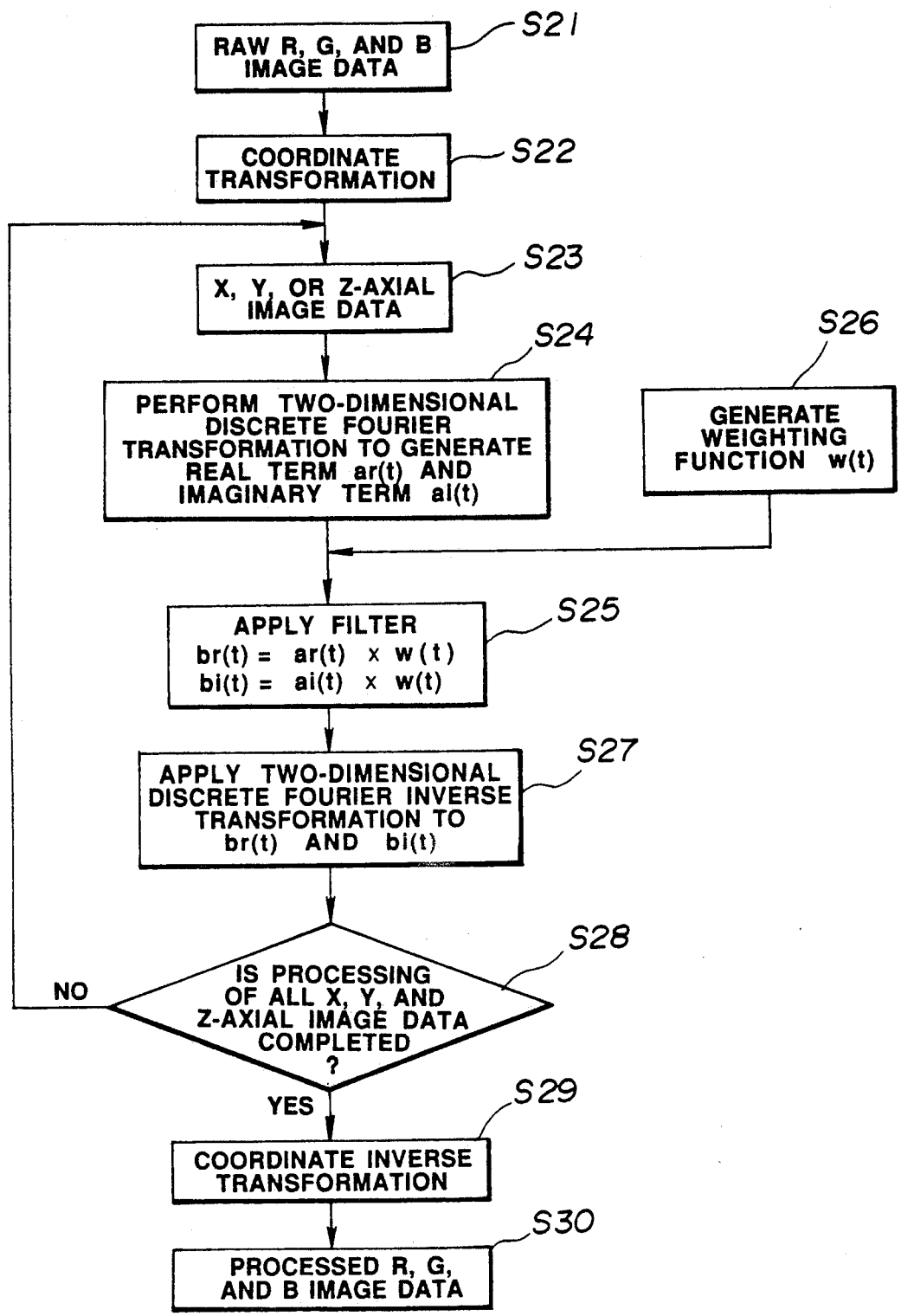
Figure 8:
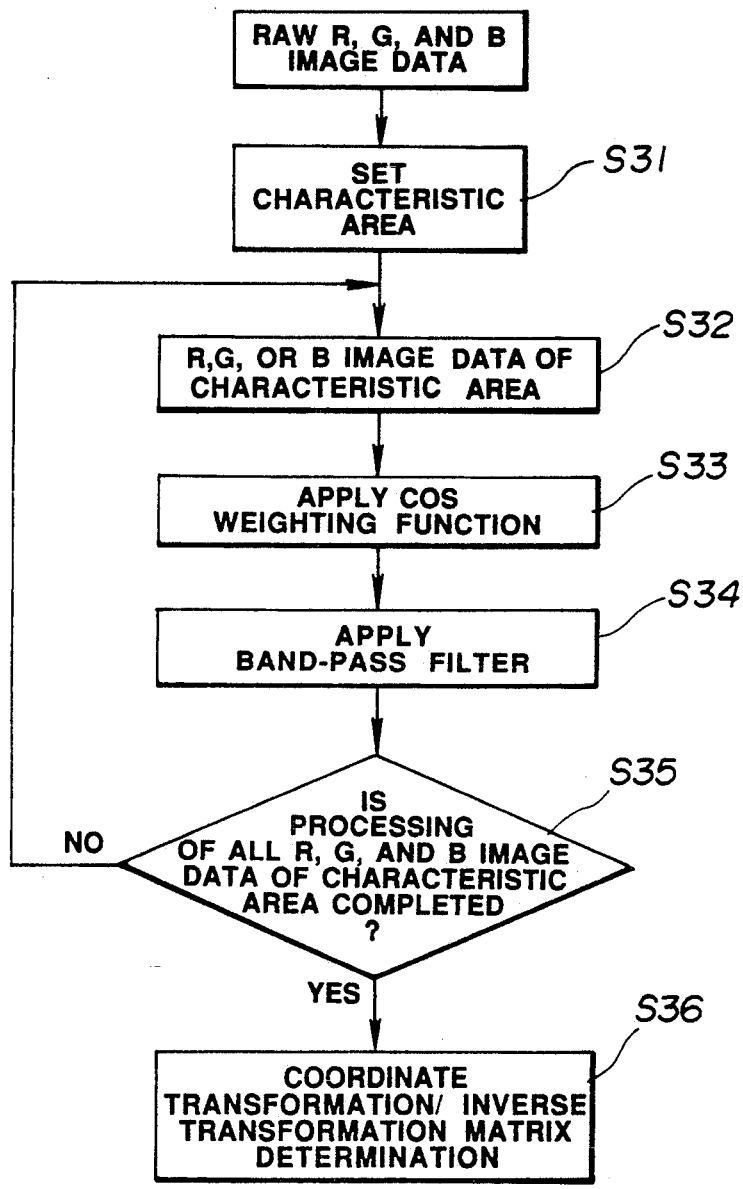

The image processor 104 inputs R, G and B image signals from memories 36a, 36b and 36c at a step S21 in FIG. 7 and comprises processing divisions for applying coordinate transformation to the R, G and B images at a step S22., and for performing two-dimensional discrete Fourier transformation at a step S24, filtering at a step S25, two-dimensional discrete Fourier inverse transformation at a step S27, and coordinate inverse transformation at a step S29. The image processor 104 also includes, as shown in FIG. 8, processing division for setting a 3 ×3 matrix for coordinate transformation at a step S31 and the inverse matrix at a step S36. The image processor 104 handles R, G and B image signals retrieved from the memories (1) 36a to (3) 36c. For the two-dimensional discrete Fourier transformation or inverse transformation of this embodiment, the coefficient shall be arranged in the same manner as those for optical Fourier transformation. That is, DC components are always arranged in the center of image data.

In general, variation in density information forming an endoscopic image acquired without using stain is great in the R image or mainly in low-frequency components. Actual information concerning a fine characteristic on the mucosal surface of an organ tends to be more dependent on the G and B images. Density information shows different distribution depending on each image. For example, when indigo carmine is used as stain, a great deal of characteristic information is sometimes contained in the R image.

Figure 11:
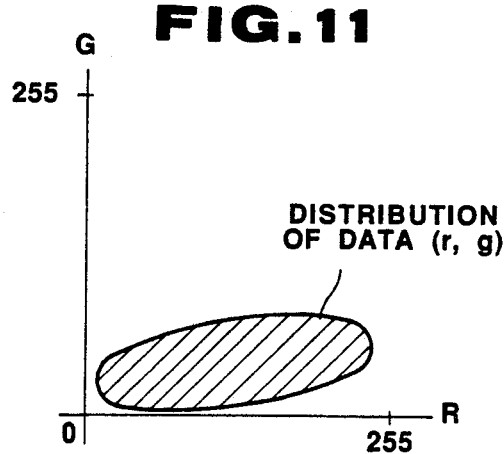

FIG. 11 shows the concept of correlational distribution of R and G data in pixels of an 256-level gradation image. Herein, a density is treated as two-dimensional data for accurate explanation. The two-dimensional data has a similarity with actual (not illustrated) B or G data. The distribution of density information shown in FIG. 11 includes all low and high-frequency components of an image. Information showing a characteristic on the mucosal surface of an organ (hereafter, characteristic component) resides in high-frequency components of a certain band. This embodiment focuses on this fact and applies band-pass filtering to extract the band likely to contain the characteristic component.

Figure 12:
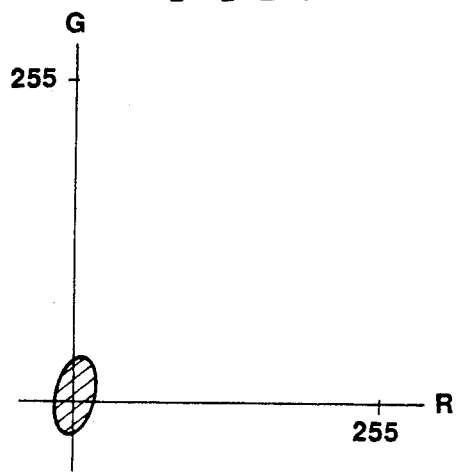

FIG. 12 shows the concept of correlational distribution observed after the band-pass filter is applied to the R and G data of FIG. 11. In a normal endoscopic image, many frequency components forming the characteristic are contained mainly in G (and B) images. Therefore, after the band-pass filtering is applied, the correlational distribution depends more greatly on the variation of G data than R data. The correlational distribution varies depending on image data. In image data acquired using stain (for example, indigo carmine), since the stain has a nature of being absorbed in red, an R image contains more characteristic components than G and B images. To enhance characteristic components of raw image effectively to be processed, the statistical distribution of the selected characteristic components is obtained and three axes substituted for the R, G and B images are set, then the results of converting raw image data relative to these coordinate axes are enhanced. An example of specific processing is described below.

Figure 9:
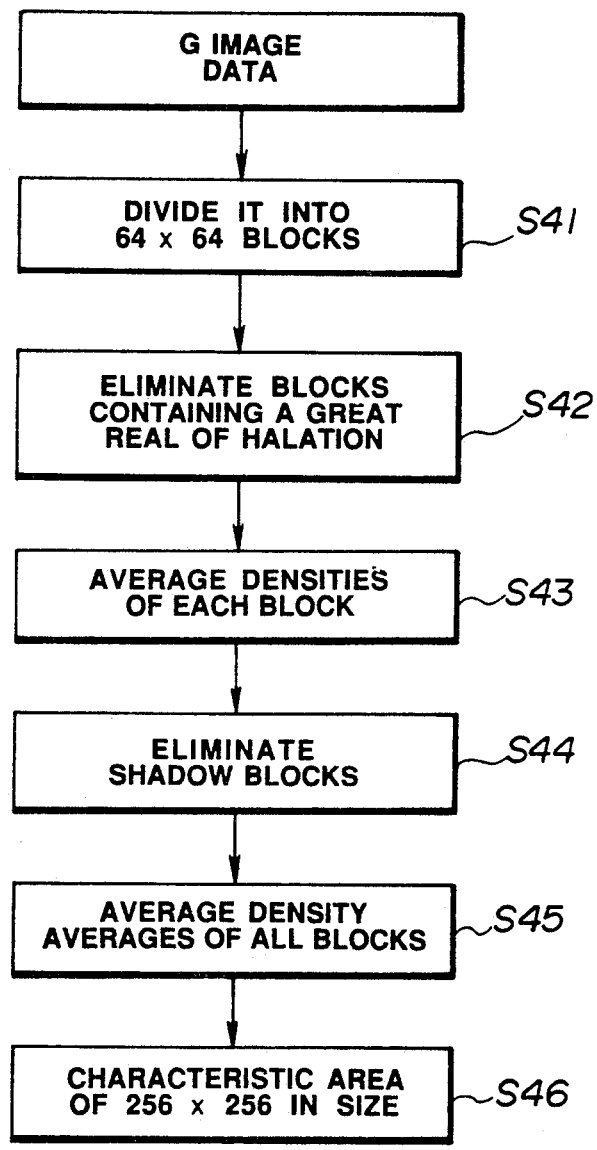

In R, G and B raw images, the most characteristic region or a region required to be enhanced is included in the center, for example, an area of 256×256 in size (hereafter, characteristic area) is set at a step S31 in FIG. 8. The center point of an image of 256×256 in size shall be a pixel corresponding to (128, 128). The characteristic area can not only be selected based on the operator's subject but also be set automatically. The flowchart shown in FIG. 9 is an example of setting a characteristic area automatically.

Figure 16:
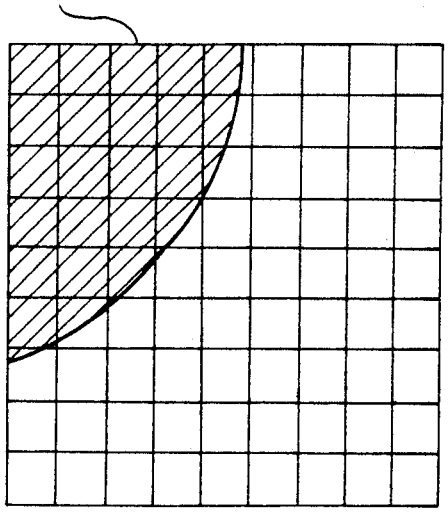

Using the property that the greatest number of characteristic components of a normal endoscopic image is contained in the G image (hereafter, G image also refers to B image), a characteristic area bringing about a coordinate transformation matrix enabling effective enhancement is set. First of all, the G image of a raw image is divided into blocks of, for example, 64×64 in size at a step S41 as shown in FIG. 9. A certain block is extracted as the center of the characteristic area from the blocks. That is to say, blocks containing halation exceeding a certain percentage are excluded from the center candidates of the characteristic area at a step S42. Then, at a step S43, the densities of the blocks which have not been excluded at the step S42 are averaged. At this time, halation components are removed from the blocks. At a step S44, blocks which have a smaller density average than a certain value, cause a shadow in an image, and are considered unsuitable for use in the characteristic area are excluded from the center candidates. In the example of FIG. 16, a block D indicated with a slanted line causes a shadow. After the series of operations is completed, the density averages of each block which is not excluded are calculated at a step S45. A block having a density average closest to the calculated value is defined as the center of the characteristic area. Then, the 256×256 characteristic area including the block as the center is extracted at a step S46. If a selected block cannot provide the data satisfying the area of 256×256 in size, a block which has a density average close to the calculated value and can extract the characteristic area is adopted as the center.

R, G and B data of each pixel in the characteristic area is acquired at a step S32 in FIG. 8, then multiplied by a cos function or a weighting function according to the following formula (1). In the function, 1 is set at the center of an image at a step S33, and when a distance from the center (corresponding to the number of pixels) n is 128, 0 is set.

$$wc(n) = 0.5 \times \cos(n\pi/128) + 0.5 \qquad (1)$$

Figure 13A:
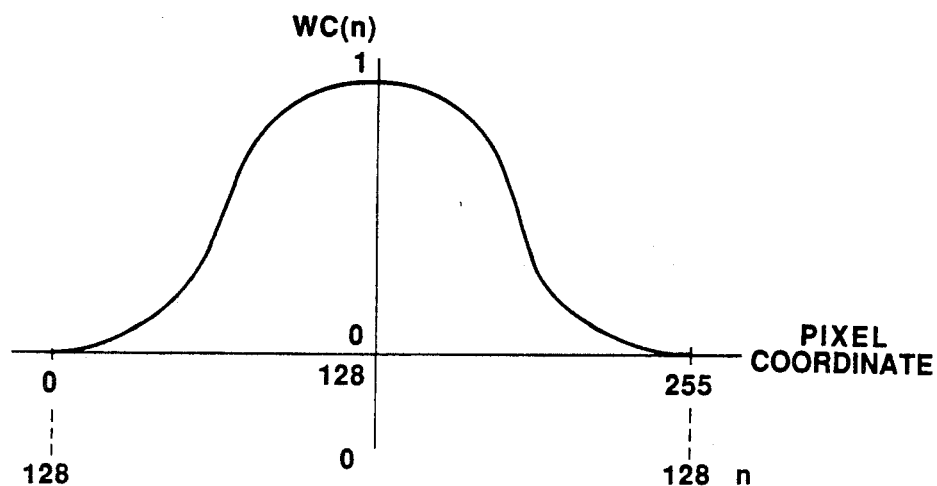
FIGS. 13a and 13b are explanatory diagrams showing weighting using a cos function.
Figure 13B:
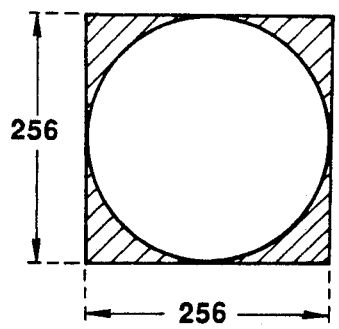
Figure 14:
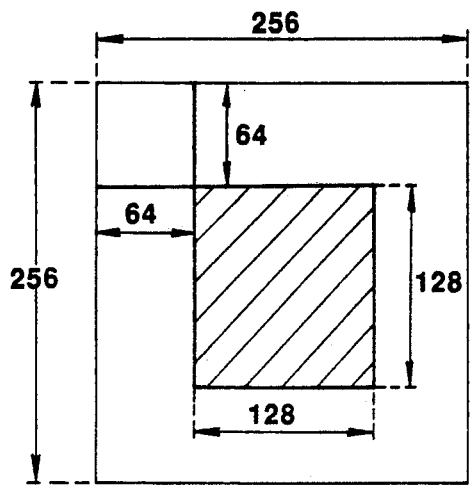

FIG. 13(a) shows the change in the weighting value that varies depending on the pixel on a segment passing through the center of a characteristic area image. For an area indicating n > 128 in the shaded part of FIG. 13(b), all the pixels are given a weighting value 0. That is, the weighting function wc(n) of the formula (1) provides the same value as the pixels along a concentric circle with respect to the center of an image. The circle shown in FIG. 13(b) represents a point at n = 128, and the shaded part, a region of n > 128. According to the formula (1). weights are placed in an area of n ≦ 128. Any point beyond n ≦ 128 is multiplied by 0 unconditionally. This operation minimizes the occurrence of distortion in an image due to the discontinuity in the data of the peripheral area resulting from band-pass filtering mentioned later.

Figure 10:
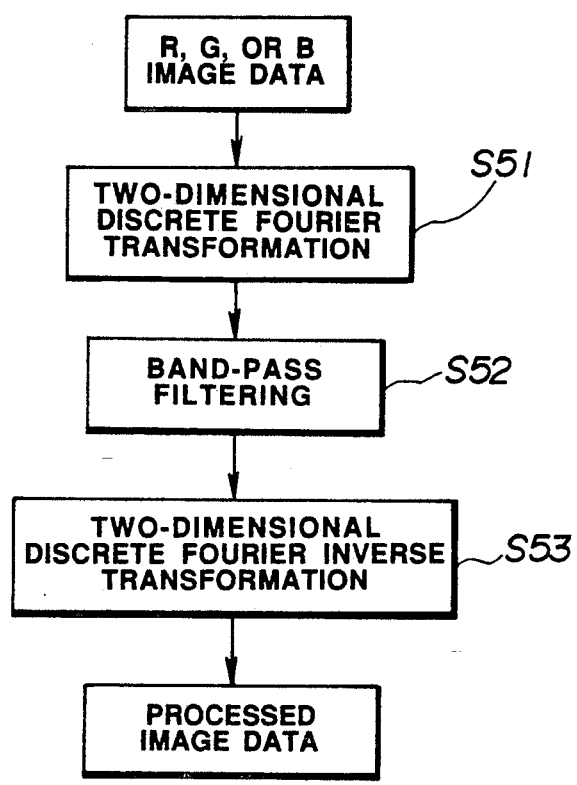
Figure 15:
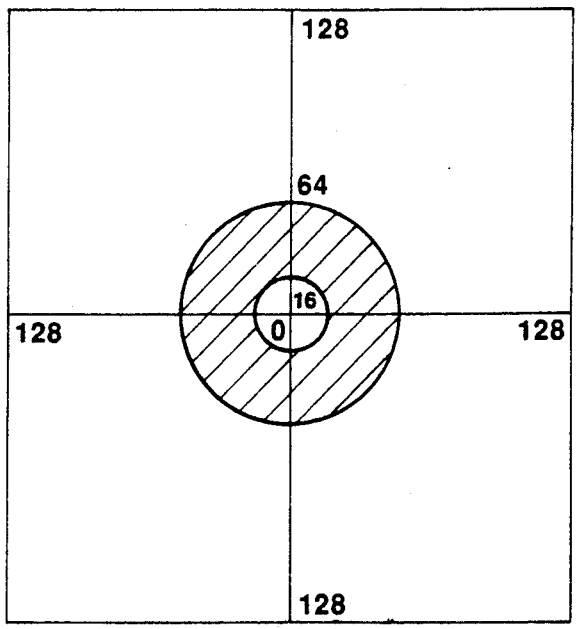

The image data of the characteristic area weighted by the cos function at the step S33 in FIG. 8 is processed by band-pass filtering at a step S34. FIG. 10 is a flowchart showing a specific example of the operation of the band-pass filtering. Each of R, G and B image is processed by two-dimensional discrete Fourier transformation at a step S51 in FIG. 10. Then, filtering having, for example, the band-pass characteristic shown in FIG. 15 is applied. A frequency band which is thought to contain a greatest number of characteristic components of endoscopic image is set as a band to be passed. Next, two-dimensional discrete Fourier inverse transformation is performed at a step S53 in FIG. 10. The image of 128×128 area (hereafter, characteristic image) including the center of the image, which is obtained by the operation described previously, is used to draw out a coordinate transformation matrix. The obtained image contains only the characteristic components extracted from a raw image. The concept of correlational distribution of R, G and B data is subject to, for example, that in FIG. 12. At a step S35 of FIG. 8, it is checked whether processing of all the R, G and B images of the characteristic area are completed or not. If completed, the processing advances to the next step.

At a step S36 in FIG. 8, coordinate transformation/inverse, transformation matrix determination using Karhunen-Loève ("KL") . . . , transformation is applied to the characteristic image obtained as described previously in order to obtain the statistical distribution of R, G and B data in the characteristic components. KL transformation is used to mechanically draw out a new system of orthogonal functions based on the statistical distribution of input image data. KL transformation is detailed in a reference entitled *Digital Image Processing Engineering* pp. 38–43, written by Kei Tezuka, Tadahiro Kitahashi and Hideo Ogawa, published by The Nikkan Kogyo Shimbun Ltd. The description, therefore, is omitted here. When the step S36 is completed, three three-dimensional vectors used for coordinate transformation are obtained. The eigen values of the vectors are compared to define X, Y and Z axes to be used as transformed coordinate axes. That is to say, the vector having the largest eigen value is defined as the X axis, and that having the smallest eigen value, as the Z axis. If the vectors defining the X, Y and Z axes are a vector ax (a11, a12, a13), a vector ay (a21, a22, a23), and a vector az (a31, a32, a33), respectively, coordinate transformation from the R, G and B data space to the space configured by the new three axes X, Y and Z is achieved by performing a matrix operation according to the following formula (2):

$$\begin{pmatrix} a11 & a12 & a13 \\ a21 & a22 & a23 \\ a31 & a32 & a33 \end{pmatrix} \begin{pmatrix} r \\ g \\ b \end{pmatrix} = \begin{pmatrix} x \\ y \\ z \end{pmatrix} \qquad (2)$$

Herein, assuming that the 3×3 vector matrix in the formula (2) is a matrix M1, coordinate inverse transformation is performed by multiplying X, Y and Z-axial data by an inverse matrix for the matrix M1.

At a step S21 in FIG. 7, the coordinate transformation matrix generated at the step S36 in FIG. 8 is used to perform the operation of the formula (2), thus, the data of each pixel (r, g and b) in R, G and B raw images is converted into (x, y, z) data.

At a step S24 in FIG. 7, each of X, Y and Z-axial pixels is subjected to two-dimensional discrete Fourier transformation.

The filtering generated at the step S25 is applied by multiplying the real term ar(t) and imaginary term ai(t) of the data generated by two-dimensional discrete Fourier transformation at the step S24 by the weighting function generated at a step S26 mentioned later. The weighting function provides X, Y and Z-axial pixels with appropriate weights. To be more specific, filtering having an enhancement effect is applied to, for example, the X image containing a great number of characteristic components, and a weighting function which performs filtering having a noise suppression effect, to the Y and Z image.

After filtering is completed at the step S26, two-dimensional discrete Fourier inverse transformation is performed at a step S27. Finally, X, Y and Z-axial pixels enhanced are obtained.

The weighting function used in the filtering at the step S26 is processed below.

In so-called optical Fourier transformation, DC components determining an overall density of an image are positioned in the center of a spatial-frequency plane, and low-frequency components relative to spatial frequencies reside in the vicinity of the DC components. A filter to be produced shall enhance a point at a distance from the center most intensively and lighten weights for low and high-frequency components gradually from a boundary of the point. Various kinds of weighting functions are thought to have this property. The filter shown below is one of the weighting functions.

Assuming that the coordinates of the center O on a spatial-frequency plane is (u0, v0), and the point of interest P on the same plane, (u,v), the distance x of OP is given by $$x = \{(u-u0)^2 + (v-v0)^2\}^{\frac{1}{2}}.$$

When a weighting value is w, w is expressed as a function w(x) of x. The w(x) value must be equal to or lager than 0, and equal to or smaller than $\alpha$. $\alpha$ is a maximum weighting value. If the center of a circle formed by a set of points yielding the maximum w(x) value is 0 and the diameter of the circle is p, the filter to be created here consists of two different functions for use under the conditions of $0 \leq x < p/2$ and $p/2 \leq x$ respectively. A cos function is used in $0 \leq x < p/2$, while a normal distribution function, in $p/2 \leq x$.

In the cos function of a filter to be created, A is specified as the amplitude. The cos function division shall be continuous at $x=p/2$ and at the normal distribution function division and represented as $w(p/2)=\alpha$. The cos function must yield a minimum value at $x=0$. A formula (3) below is generated as a function meeting these conditions:

$$w(x) = \alpha - A - A \times \cos\{X \times \pi/(p/2)\} \quad (3)$$
$$(0 \leq x < p/2)$$

The function of the formula (3) provides a maximum value $\alpha$ at $x = p/2$ and a minimum value $\alpha - 2A$ at $x=0$ (center of a spatial-frequency domain). When $\sigma$ is specified as a standard deviation in this kind of function, the following formula (4) is obtained:

$$w(x) = \alpha \times \exp[-0.5\{(x - (p/2))/\sigma\}^2] \quad (4)$$
$$(p/2 \leq x)$$

In the formula (4), $\sigma$ is given according to $\sigma=(CTR-(p/2))/r$ (where, CTR represents the x coordinate value of the center, and r, a real number). For $p=0$, only equation (4) can be adopted. In either the formula (3) or (4), when $\alpha$, A, p and r are specified as parameters, filters permitting different levels of enhancement can be obtained by changing the parameter values. FIG. 15 shows an example of a filter characteristic generated under the aforesaid conditions. For example, $\alpha=4$, $A=1.5$, $p=60$ and $r=4$ are specified. To realize filtering permitting a noise suppression effect, high-frequency components considered to contain a great number of noise components must be suppressed. Therefore, for example, $\alpha=1$, $A=0$, $p=0$ and $r=3$ can be set. To realize filtering permitting an image enhancement effect, a frequency band presumably containing a great deal of structural pattern information of raw image data must be enhanced and the band must be suppressed. Therefore, for example, $\alpha=3$, $A=1$, $p=50$ and $r=4-7$ can be set.

At a step S28 in FIG. 7, it is checked if all processing steps by the step S27 for X, Y and Z-axial pixels are completed. After the completion, coordinate inverse transformation is performed at a step S29. As a result, enhanced R, G and B images are obtained. Specifically, according to the inverse matrix M2 of the matrix M1, the processing steps can be applied to (X', Y', Z') data of the above processed pixels by the formula (5) below.

$$\begin{pmatrix} b11 & b12 & b13 \\ b21 & b22 & b23 \\ b31 & b32 & b33 \end{pmatrix} \begin{pmatrix} x' \\ y' \\ z' \end{pmatrix} = \begin{pmatrix} r' \\ g' \\ b' \end{pmatrix} \quad (5)$$

Again, after the flowchart returns to R, G and B images, (r', g', b') data of each pixel can be obtained by the aforesaid operation at a step S30 in FIG. 7. Then, the result of R, G and B operation is displayed as an image on the monitor 106 shown in FIG. 1.

In this embodiment, a fine pattern on the mucosal surface is enhanced for R, G and B raw images in the image processor 104 and at the same time, a clear image in which noise is suppressed can be obtained.

For the aforesaid operation, a noise elimination process (for example, using a median filter having a $3 \times 3$ mask size) can be applied as the previous process for the raw images.

An automatic setting method of characteristic areas is not restricted to the example in this embodiment and various methods can be considered. A method of determining a coordinate transformation matrix at a step S36 in FIG. 8 is not restricted to KL transformation. If the method draws out a coordinate transformation matrix adapted to the processed subject image, the method is usable appropriately. The operation in the embodiments can be realized as parallel operation. The matrices in the embodiment is not obtained in accordance with the images one by one. For example, a matrix previously drawn out can be applied depending on the difference on the distribution of an R image.

In the aforesaid embodiments, enhancement or noise suppression operation using two-dimensional discrete Fourier transformation or weighting functions shown in S1-S3 in FIG. 4, S13-S15 in FIG. 6 and S24-S27 in FIG. 7, or the band-pass filtering shown at the step S34 in FIG. 8 can be realized as mask operation. Also, the weighting according to the cos function at the step S33 in FIG. 8 is not needed.

Figure 17:
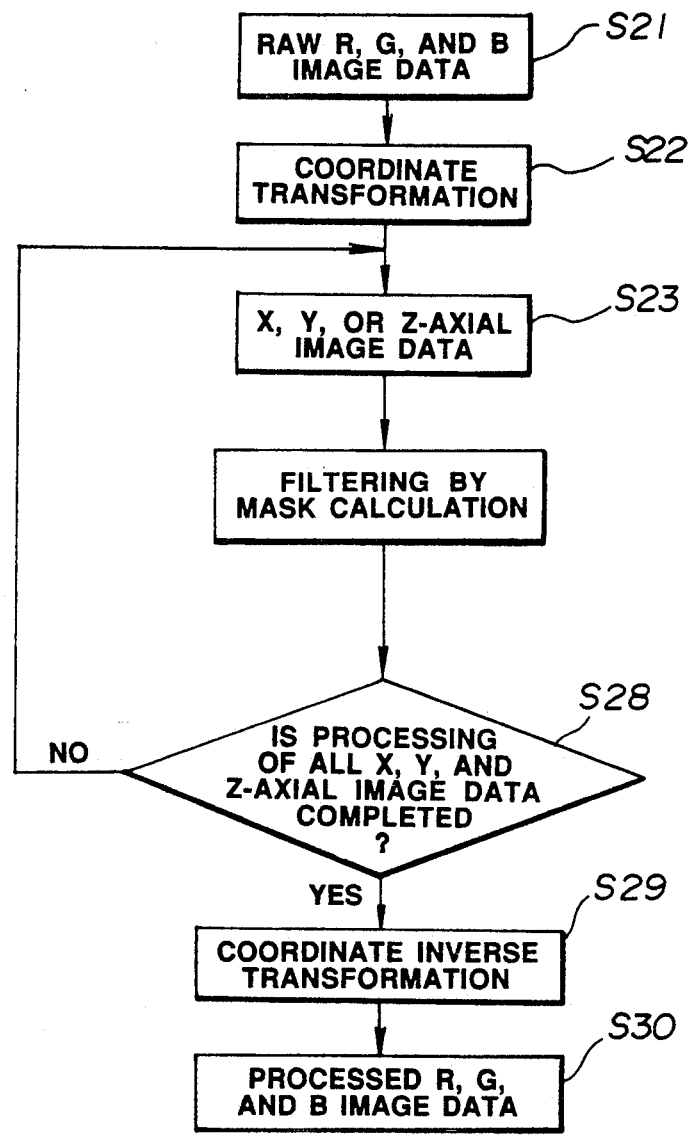

For example, the operation of FIG. 7 can be replaced with that of FIG. 17, and that of FIG. 8 can be replaced with that of FIG. 18. The mask operation used for convolution may be applied. The band passing characteristic of the mask operation is similar to the filtering operation in the aforesaid embodiments. Setting the mask operation is described, for example, in a reference entitled "A Computer Program for Designing Optimum FIR Linear Phase Digital Filters" written by James H. McClellan, *IEEE Transaction on Audio and Electoacoustics*, Vol. AU-21, No.6, pp.506-626, December 1978 or a reference entitled "Designing of Two-Dimensional FIR Fan Filters by Fourier Reconstruction" in *The Transactions of the IECE of Japan*, Vol. B63, No. 12, pp. 849-854, December 1980.

What is claimed is:

1. An endoscopic image processor comprising:
    color signal transforming means for setting a group of vectors for transforming each signal of an endoscopic image, resolved into a plurality of color signals, into a plurality of first new color signals based on statistical characteristics of the image and transforming the color signals of said endoscopic image into first new color signals by a use of a first matrix in a first matrix operation using said group of vectors;
    filtering means for filtering the plurality of said first new color signals produced by said color signal transforming means; and
    transforming means for transforming said plurality of first new color signals after said filtering means applied filtering to the new color signals into a plurality of second new color signals corresponding to said original color signals by a second matrix operation using an inverse matrix of said first matrix used for said first matrix operation.

2. An endoscopic image processor according to claim 1, wherein said filtering means uses at least one of an enhancement filter and a noise suppression filter.

3. An endoscopic image processor according to claim 1, wherein said filtering means determines a filter to be used based on information contained in each color signal.

4. An endoscopic image processor according to claim 1, wherein said filtering means includes noise suppression filtering for suppressing frequency components being capable of containing many noise components and image enhancement filtering for enhancing a frequency band containing a large amount of information of a structural pattern of a raw image.

5. An endoscopic image processor according to claim 1, wherein said filtering means performs filtering with a noise suppression effect for an R image in a case of ordinary R, G and B endoscopic images without using stain and applies weighting functions performing filtering with an enhancement effect to G and B images.

6. An endoscopic image processor according to claim 1, wherein said filtering means performs filtering with an enhancement effect for an axis and performs filtering with a noise suppression effect for another axis.

7. An endoscopic image processor according to claim 1, wherein the group of vectors in said color signal transforming means is set by KL transformation.

8. An endoscopic image processor according to claim 1, wherein the group of vectors in said color signal transforming means is selected to set from a plurality of groups of vectors previously prepared.

9. An endoscopic image processor according to claim 1, wherein positions in front of the color signal transforming means comprises
   characteristic area setting means for setting a characteristic area containing one of a characteristic region and a region to be desired to be enhanced from the endoscopic image resolved into the plurality of color signals,
   band-pass filtering means for applying band-pass filtering for passing only a predetermined frequency band for a characteristic area image being set in each of said color signals, and
   acquiring means for acquiring a vector by obtaining a statistical distribution of each color data of said characteristic area image passed and gained.

10. An endoscopic image processor according to claim 9, wherein said characteristic area setting means is performed manually.

11. An endoscopic image processor according to claim 9, wherein said characteristic area setting means comprises
   dividing means for dividing a G image in the endoscopic image into a plurality of blocks,
   eliminating means for eliminating blocks containing more than a certain percentage of halation in the image of said divided plurality of blocks,
   calculating means for calculating a density average in each block other than said blocks to be eliminated except a halation part,
   removing means for removing blocks dissatisfying a predetermined density average in the blocks remained, and
   extracting means for calculating a density average in said blocks remained except said removed blocks and extracting a characteristic area containing a block as a center of the characteristic area, the block having a density average closest to the calculated density average.

12. A method of processing an endoscopic image comprising:
   a color signal transforming step of setting a group of vectors for transforming each signal of an endoscopic image, resolved into a plurality of color signals, into a plurality of first new color signals based on statistical characteristics of the image and transforming the color signals of said endoscopic image into first new color signals by a use of a first matrix in a first matrix operation using said group of vectors;
   a filtering step of filtering the plurality of said first new color signals produced by said color signal transforming step; and
   a transforming step of transforming said plurality of first new color signals after said filtering step applied filtering to the new color signals into a plurality of second new color signals corresponding to said original color signals by a second matrix operation using an inverse matrix of said first matrix used for said first matrix operation.

13. A method of processing an endoscopic image according to claim 12, wherein said filtering step uses at least one of an enhancement filter and a noise suppression filter.

14. A method of processing an endoscopic image according to claim 12, wherein said filtering step determines a filter to be used based on information contained in each color signal.

15. A method of processing an endoscopic image according to claim 12, wherein said filtering step includes noise suppression filtering for suppressing frequency components being capable of containing many noise components and includes image enhancement filtering for enhancing a frequency band containing a large amount of information of a structural pattern of a raw image.

16. A method of processing an endoscopic image according to claim 12, wherein said filtering step performs filtering with a noise suppression effect for an R image in a case of ordinary R, G and B endoscopic images without using stain and applies weighting functions performing filtering with an enhancement effect to G and B images.

17. A method of processing an endoscopic image according to claim 12, wherein said filtering step performs filtering with an enhancement effect for an axis and performs filtering with a noise suppression effect for another axis.

18. A method of processing an endoscopic image according to claim 12, wherein the group of vectors of said color signal transforming means is set based on frequency components forming a structural pattern in a raw image.

19. A method of processing an endoscopic image according to claim 12, wherein KL transformation is used as a drawing out procedure of the group of vectors in said color signal transforming step.

20. A method of processing an endoscopic image according to claim 12, wherein the group of vectors in the color signal transforming step are selected to set from a plurality of vectors previously prepared.

21. A method of processing an endoscopic image according to claim 12, wherein the endoscopic image is one of an ordinary image without using stain and an endoscopic image using stain.

22. A method of processing an endoscopic image according to claim 12, wherein, before the color signal transforming step, further comprising:
- a characteristic area setting step of setting a characteristic area containing one of a characteristic region and a region to be desired to be enhanced from the endoscopic image resolved into the plurality of color signals;
- a band-pass filtering step of applying band-pass filtering for passing only a predetermined frequency band for a characteristic area image being set in each of said color signals; and
- an acquiring step of acquiring a vector by obtaining a statistical distribution of each color data of said characteristic area image passed and gained.

23. A method of processing an endoscopic image according to claim 12, wherein said characteristic area setting step is performed manually.

24. A method of processing an endoscopic image according to claim 22, wherein said characteristic area setting step comprises
- a dividing step of dividing a G image in the endoscopic image into a plurality of blocks;
- an eliminating step of eliminating blocks containing more than a certain percentage of halation in the image of said divided plurality of blocks;
- a calculating step of calculating a density average in each block other than said blocks to be eliminated except a halation part;
- a removing step of removing blocks dissatisfying a predetermined density average in the blocks remained, and
- an extracting step of calculating a density average in said blocks remained except said removed blocks and extracting a characteristic area containing a block as a center of the characteristic area, the block having a density average closest to the calculated density average.

25. A method of processing an endoscopic image according to claim 22, wherein the endoscopic image is one of an ordinary endoscopic image without using stain and an endoscopic image using stain.

* * * * *